United States Patent [19]
Achsel et al.

[11] 3,962,315
[45] June 8, 1976

[54] PROCESS FOR THE PURIFICATION OF TEREPHTHALIC ACID DIMETHYL ESTER

[75] Inventors: Eberhard Achsel, Fischbach, Taunus; Hans-Peter Hortig, Hattersheim, Main; Heinrich Seipp; Heinz Giller, both of Offenbach, Main, all of Germany

[73] Assignee: Hoechst Aktiengesellschaft, Frankfurt am Main, Germany

[22] Filed: May 7, 1974

[21] Appl. No.: 467,833

[30] Foreign Application Priority Data
May 9, 1973   Germany............................ 2323219

[52] U.S. Cl............................................. 260/475 B
[51] Int. Cl.².................................... C07C 67/48
[58] Field of Search ................................ 260/475 B

[56] References Cited
UNITED STATES PATENTS

| | | | |
|---|---|---|---|
| 2,802,861 | 8/1957 | Dijk et al. | 260/475 B |
| 3,037,048 | 5/1962 | Lotz | 260/475 B |
| 3,502,711 | 3/1970 | Claybaugh et al. | 260/475 B |

FOREIGN PATENTS OR APPLICATIONS

| | | | |
|---|---|---|---|
| 1,296,465 | 5/1962 | France | 260/475 B |
| 1,597,677 | 12/1968 | France | 260/475 B |
| 1,017,611 | 12/1953 | Germany | 260/475 B |
| 1,125,417 | 8/1960 | Germany | 260/475 B |
| 38-469 | 1/1963 | Japan | 260/475 B |

*Primary Examiner*—Elbert L. Roberts
*Assistant Examiner*—D. R. Phillips
*Attorney, Agent, or Firm*—Curtis, Morris & Safford

[57] ABSTRACT

Crude DMT containing, as impurities mainly dimethyl isophthalate, dimethyl orthophthalate and p-toluic acid methyl ester, is purified with the use of solvents known to be useful for the recrystallization of DMT in such a manner that the crude DMT in molten state is introduced with agitation into the solvent, the temperature of which is maintained above the temperature of that eutectic mixture of DMT and the main impurities associated therewith which has the highest melting point. As soon as the solvent is saturated with DMT, pure DMT crystallizes. The process is preferably carried out continuously and in a special vertical countercurrent washing column.

3 Claims, 1 Drawing Figure

U.S. Patent  June 8, 1976  3,962,315
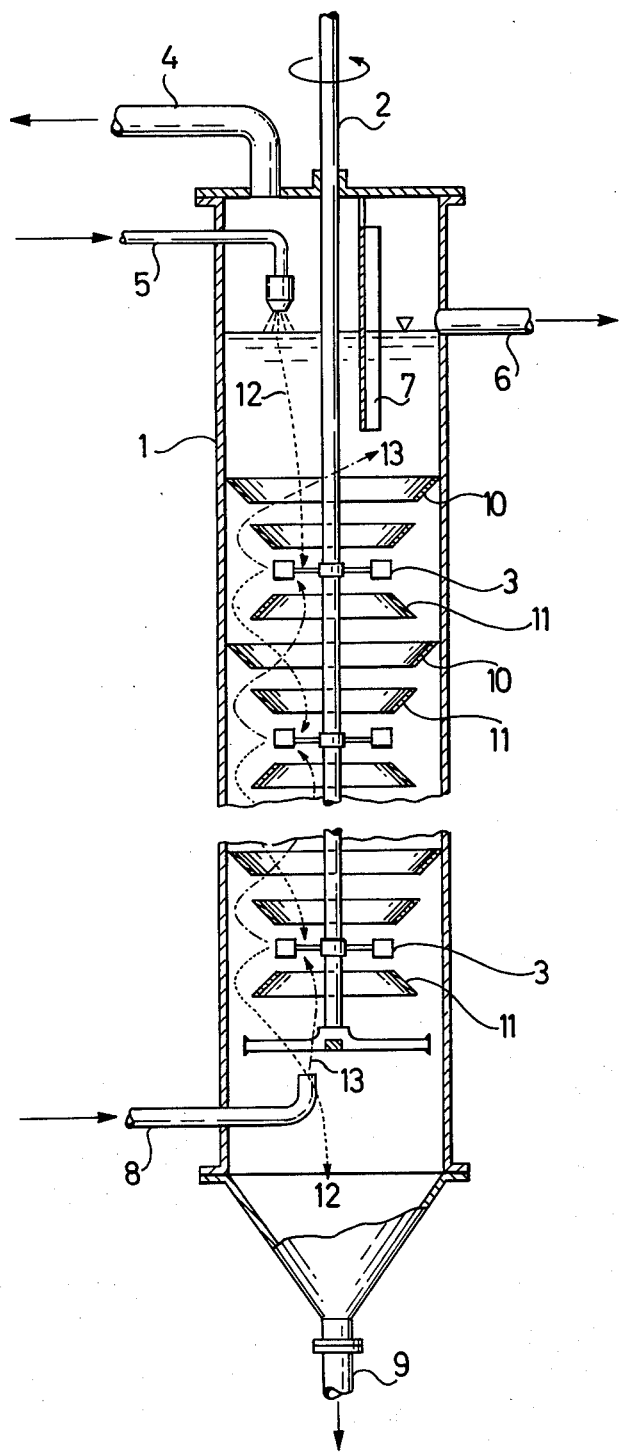

PROCESS FOR THE PURIFICATION OF TEREPHTHALIC ACID DIMETHYL ESTER

The present invention relates to a process for the purification of terephthalic acid dimethyl ester.

Terephthalic acid dimethyl ester (DMT), as starting material for the manufacture of polyester fibers, filaments, films or sheets, has to meet special purity requirements. The desired degree of purity either cannot be obtained by rectification of a DMT-containing crude ester, resulting for example from the liquid phase oxidation of p-toluic acid methyl ester and subsequent esterification, or can be obtained only with considerable expenditure of technology and energy. For this reason, recrystallization from methanol is generally used as a purification process for the preparation of DMT having a high degree of purity.

Although the state of the art provides various crystallization agents which permit continuous crystallization from solution, this crystallization process involves a considerable cost, since each recrystallization comprises four steps which are independent one of the other: that is, first, the preparation of a genuine solution, optionally with a subsequent filtration; second, the crystallization as such which is carried out by cooling and/or evaporation of the solvent; third, the separation of the crystallized substance from the solvent phase containing the impurities by filtration or centrifugation; and fourth, the washing of the crystals obtained with pure solvent. The crystallization must also be carried out in a manner which ensures the constant presence of a sufficient number of crystal nuclei, and a not too rapid growth of crystals, since otherwise impurities are incorporated into the crystals as they are formed.

It was therefore object of the present invention to provide a simple purification method which is suitable especially for the purification of DMT and permits above all a continuous operation.

This object of providing a simple and efficient process for the purification of crude DMT, containing as impurities mainly dimethyl isophthalate (DMI), dimethyl orthophthalate (DMO) and p-toluic acid methyl ester (pTE), with the use of solvents known to be useful for the recrystallization of DMT is achieved by adding the crude DMT in molten state with agitation to the solvent, the temperature of which is maintained above the temperature of that eutectic mixture of DMT and the main impurities associated therewith which has the highest melting point. As soon as the solvent is saturated with DMT, pure DMT crystallizes. The impurities remain in molten state in the form of an eutectic and are separated from the pure crystals by the solvent.

The substances DMI, DMO, and pTE identified as main impurities of the crude DMT are for example present in the case where the DMT is prepared according to the so-called Katzschmann process by liquid phase oxidation of p-xylene or p-xylene/pTE with oxygen or air and subsequent esterification. Other impurities which may also be present in this DMT in very small amounts can be neglected, since they dissolve generally in the solvents used and thus do not crystallize together with the pure DMT.

The process of the invention for the purification of crude DMT containing DMI, DMO and pTE as main impurities may in principle be applied also to the purification of a DMT having other main impurities and, generally, to the purification of contaminated solids which melt without decomposition, inasmuch as the phase diagram of the mixture in question is known or may be evaluated, so that the position of the eutectics and thus the temperature of the solvent may be determined.

As solvents for the process of the invention, practically all organic or aqueous-organic solvents known to be useful for the recrystallization of DMT may be used, for example benzene and the homologues thereof (toluene, xylenes, etc.), aliphatic hydrocarbons having from 3 to about 10 carbon atoms (when the lower hydrocarbons which become gaseous under atmospheric pressure are used, operations are carried out under pressure), aromatic, aliphatic or cyclo-aliphatic alcohols, ketones, ethers, esters or acids. The compounds may also have inert substituents such as halogen atoms (chlorinated hydrocarbons !). Methanol is the preferred solvent. Of course, also mixtures of the cited solvents may be employed.

One condition for a successful DMT purification according to the process of the invention is to maintain the solvent at a temperature which is above the temperature of that eutectic mixture formed by DMT and the main impurities associated therewith which has the highest melting point, since at a lower temperature not only pure DMT but also all kinds of mixed crystals and crystal mixtures precipitate. For example, the eutectic of the binary system of DMT/pTE is at 28°C, and it contains 4 % of DMT; the eutectic of the system of DMT/DMI solidifies at 64°C and contains 2 % of DMT. When a melt of DMT and DMO/DMI/pTE (weight ratio 1 : 5 : 1) is allowed to solidify, pure DMT crystallizes at 61°–62°C, and the remaining melt contains only 5 % of DMT. When the process of the invention is applied, the temperature of the solvent should therefore not be below about 65°C because of the position of the different eutectics. Thus, in this case, at a temperature above 65°C, the crystallization of practically pure DMT is ensured.

By adding the hot melt of crude DMT to the solvent, and by the heat generated during the crystallization of the DMT, the temperature of the solvent rises to an indesirable extent. It is therefore advantageous to control the pressure over the solvent in such a manner that portions of the solvent are always able to evaporate and thus remove heat. The solvent evaporated and recondensed in a cooling system, for example a reflux condenser, is subsequently recycled into the crystallization solution. Of course, it is also possible to control the temperature of the solution system by a conventional exterior cooling or the like of the receptacle or vessel where the crystallization is carried out.

The purification process according to the present invention may be carried out continuously or batchwise. It is especially advantageous to use a continuous operation in which crude DMT melt and solvent may be constantly fed into a conventional vessel provided with an agitator, from which pure crystallized DMT is constantly discharged; this DMT being mixed with the solvent containing the impurities. This contaminated solvent may be easily separated from the DMT (for example by washing).

The solvent in the crystallization vessel always remains saturated with DMT.

It is especially advantageous to carry out the process continuously in a vertical counter-current washing column provided with an agitator device; a condenser, a melt inlet and a solvent outlet in its upper part; and at least one solvent inlet and a product outlet in its lower part. With constant agitation, crude DMT melt is constantly fed in via the melt inlet, pure solvent is fed via the solvent inlet, the impurities-containing solvent is discharged via the solvent outlet, and crystallized pure DMT is discharged via the product outlet. In this mode of operation it has proved to be especially advantageous to use a paddle agitator in the vertical counter-current washing column, and to provide this column with frusto-conical interior wall baffles and frusto-conical guide plates alternately inclined upwards and downwards, which guide plates have central openings of about the size of the paddles and are solidly fixed to the column wall in such a manner that there is a distance between them and the column walls which is about the same as the horizontal projection of the frusto-conical wall baffles.

The especially advantageous embodiment of the purification process of the invention which is carried out in a vertical counter-current washing column will be more clearly understood by reference to the accompanying drawing. The vertical counter-current washing column 1 is provided with a paddle agitator 2 having paddles 3 as agitating elements. At the top of the column, there is an outlet 4 which is connected to a conventional condenser (not shown in the drawing). The column is provided in its upper part with a melt inlet 5 and a solvent outlet 6. The stabilizing plate 7 serves to stabilize possible turbulences of the liquid in the column. The lower part of the column is provided with a solvent inlet 8 and a product outlet 9. If desired, further solvent inlets may be arranged above solvent inlet 8. The interior wall of the column is provided with frusto-conical wall baffles 10 and frusto-conical guide plates 11 alternately inclined upwards and downwards. The guide plates 11 are solidly fixed to the column wall by connecting rods or similar devices (not shown in the drawing).

For the purification operation according to the present invention in this vertical counter-current washing column, pure solvent is constantly fed in via solvent inlet 8, and, having absorbed the impurities from the crude DMT, discharged via solvent outlet 6. The crude DMT is introduced into the column via melt inlet 5 and thus continuously fed into the solvent being agitated. The crystallization substantially takes place immediately after the melt has been introduced dropwise into the solvent, so that the upper part of the column may be defined as a crystallization zone. Because of the specific gravity difference between the DMT crystals and the liquid in the column, the DMT crystals move downwards from the crystallization zone into the agitation range of paddle agitator 2, where intense mixing with the current of the solvent moving in the opposite direction (upwards) takes place. The mixing zone comprises a radially acting, bilaterally aspirating paddle wheel having a vertical axle, the paddle location of which causes the formation of a turbulence zone providing effective mixing of the solids and liquid, and the conveyance of the mixtures in radial direction. By means of the fixed frusto-conical guide plates 11 mounted above and below the paddles 3, the current liquid mixture ejected by the paddles 3 is led outward in a path that diverges both radially and axially, and thus the flow rate decreases on account of the increase of the cross section of the flow rate. With decreasing flow rate, the entraining force of the liquid exerted on the solid particles also decreases, and the influence of the specific gravity difference between the solid and liquid begins to become the decisive influence governing the movement of the particle, while the liquid, which is continuously fed in, moves in the opposite direction from the separation zone, and thus both the solid and liquid flow again in their original direction. Depending on the desired purification effect, the number of these process steps or stages in series-connection may vary. It is necessary to guide the streams emerging coaxially in the vicinity of the circumference of the baffles to the axial aspirating sections of the paddles of two neighboring stages, which is carried out in this case by vertical series-connection of the stages with interposition of further fixed frustum-shaped guide devices, that is, frusto-conical wall baffles.

The minimum number of the described stages depends on the desired purification effect and on the solids/solvent ratio. There is practically no upper limit for the number of stages. Above DMT outlet 9 at the lower end of the column, there is a thickening zone as usual. The product is discharged either by free falling or by means of a known discharging device, for example a slurry pump.

The lower limit of the rotational speed of the agitator is governed by the corresponding decrease of the turbulence because of a lower circumferential speed of the paddles. The maximum number of revolutions is limited by the volume of the stabilizing zone in the vicinity of the solvent outlet.

When the column operates, the DMT follows approximately the path illustrated by the dotted line 12 and the solvent follows the path illustrated by the dotted line 13. The solvent which evaporates because of the liquid phase being heated by the hot crude DMT melt introduced, by the heat of crystallization after passing through duct 4 to the reflux condenser, and is recycled into the column.

The following examples illustrate the invention.

EXAMPLE 1

2000 ml of methanol (= 1600 g) are introduced into and heated to boiling in a four-necked flask having a capacity of 3 l and provided with agitator, reflux condenser, thermometer and heatable dropping funnel. With homogeneous agitation, 800 g of DMT melt, contaminated by 10 % of DMI, are added dropwise to this solvent. Until saturation the DMT dissolves, and thereafter it crystallizes directly to uniform little plates. The methanolic phase containing the impurities is poured off in hot state, the crystallized DMT is washed with hot methanol, suction-filtered and dried. The purity of the DMT so obtained is exceptionally high; the analysis result is <30 ppm of DMI.

EXAMPLE 2

As described in Example 1, 800 g of DMT melt, contaminated by 9.2 % of DMI and 3.8 % of DMO, is added dropwise to the boiling solvent mixture of 450 g of pTE and 1450 ml (= 1150 g) of methanol. The crystals formed are washed with hot methanol, suction-filtered and dried. The analysis result is 750 ppm of pTE, 20 ppm of DMO and <30 ppm of DMI.

EXAMPLE 3

As described in Example 1, 800 g of DMT melt, contaminated by 1.0 % of DMO, 5.4 % of DMI and 1.2 % of pTE, are added dropwise to the boiling solvent mixture of 1280 g of methanol and 320 g of methylene chloride (boiling point at 760 torrs 55.5°C). The crystals formed are washed with hot methanol, suction-filtered and dried. The analysis result is <20 ppm of DMO, <20 ppm of DMI, 40 ppm of pTE.

EXAMPLE 4

In a counter-current washing column used as a crystallizer (as shown in the accompanying drawing) having a diameter of 220 mm, provided with 12 agitating zones, and a reflux condenser, 98 kg per hour of crude DMT melt containing 93 % of DMT, 1 % of DMO, 5 % of DMI and 1 % of pTE are fed in at the top via a feeding jet, pumped by means of a gear pump. The agitation zones are produced by rotating paddles which are mounted an a common shaft. The paddles vigorously mix the solid and the liquid phase and radially convey the mixture to the surrounding stabilization zones. While the crystallized DMT in the lighter methanolic phase sinks downwards and, passing the frusto-conical guide plates and the frusto-conical wall baffles, falls into the suction zone of the next mixing stage, the methanolic phase is forced to flow in a counter-current direction by pumping 304 kg per hour of fresh methanol into the suction zone of the lowest paddles, and by discharging 116 kg per hour of methanolic solution via the solvent outlet at the top of the column. The methanolic phase enters the different agitation zones at the suction face of the paddles and flows through the sinking DMT crystals. The bottom of the column serves as a thickening zone, from which, by means of a screw pump, 286 kg per hour of suspension having a solids content of 29 % are discharged.

After centrifugation and drying, the DMT so obtained contains 3 ppm of DMI, 2 ppm of DMO and 6 ppm of pTE.

What is claimed is:

1. A process for the purification of crude dimethyl terephthalate (DMT) made by the oxidation of p-xylene or p-xylene/p-toluic acid methyl ester (pTE) and subsequent esterification and containing as impurities dimethyl isophthalate (DMI), dimethyl orthophthalate (DMO) and (pTE) which comprises adding crude molten dimethyl terephthalate to a body of methanol to form a mixture of said crude DMT and a saturated solution of DMT in said methanol, maintaining the mixture of DMT and methanol solution at a temperature above the melting point of the eutectic mixture of DMT and DMI, DMO and pTE having the highest melting point, vigorously agitating the mixture of DMT and methanol solution, continuing to add crude molten DMT to said mixture to cause relatively pure DMT to crystallize therefrom and to cause the impurities to dissolve in said solution.

2. A process according to claim 1 wherein said mixture of methanol solution and DMT is maintained at a temperature of at least 65°C.

3. A process according to claim 1 wherein crude molten DMT and fresh methanol are continuously added to said mixture and pure crystallized DMT admixed with methanol solution is continually removed from said body of said solution.

* * * * *